United States Patent [19]
Liedholz

[11] 3,977,794
[45] Aug. 31, 1976

[54] UNIVERSAL CELL HOLDER
[75] Inventor: Gerhard A. Liedholz, Miami, Fla.
[73] Assignee: Coulter Electronics, Inc., Hialeah, Fla.
[22] Filed: July 15, 1974
[21] Appl. No.: 488,753

[52] U.S. Cl. .............................. 356/244; 356/201
[51] Int. Cl.² ........................................ G01N 21/16
[58] Field of Search ........... 356/244, 246, 256, 201, 356/204–208, 96, 180, 181; 250/576, 573, 575; 248/311, 313, 314, 316 B

[56] References Cited
UNITED STATES PATENTS

| 3,551,062 | 12/1970 | Brown | 356/244 |
| 3,567,328 | 3/1971 | Riley | 250/576 |
| 3,711,201 | 1/1973 | Sturlese et al. | 356/244 |

Primary Examiner—Vincent P. McGraw
Assistant Examiner—Jon W. Henry
Attorney, Agent, or Firm—Silverman & Cass, Ltd.

[57] ABSTRACT

A universal holder for objects such as test tubes, cuvettes, cells and the like comprising a stationary upright body having a pair of angularly arranged planar surfaces, the surfaces defining a V-shaped recess and a deflectable spring-biased member arranged for pivotal movement against its bias from a normally horizontal disposition extending into the aforesaid recess and the biased member capable of being deflected by the object as it is introduced in the recess. The planar surfaces may have matching elongate notches to provide a purchase for angular bodies, such as rectangular cells. Both the upright body and the deflectable member have slot means arranged to permit a light beam freely to pass therethrough and through the object.

31 Claims, 11 Drawing Figures

UNIVERSAL CELL HOLDER

FIELD OF THE INVENTION

This invention relates generally to apparatus for use in making physical measurements in the medical, biological and industrial field and more particularly is concerned with the positioning of cells, particularly for use in examining and analyzing phenomena by photometric procedures.

Particularly in the field of photometric analysis, that is the examination and analyzing of phenomena by means of measuring either the absorbence or the transmittance of light in samples of substances being studied, many biological physical, chemical, interrelated phenomena are analyzed by the passage of light through solutions, suspensions, and fluids. The usual method employed in photometric procedures is to place the sample solution in a small cell or cuvette, the walls of which are transparent relative to the wavelength of the light being used. The cuvette is interposed between the source of the light and a photosensitive-detecting element. In such analytical procedures, the cells or cuvettes employed often are of varying size and configuration, some being rectangular, square or diagonal, and others round, the latter being in the form of test tubes and the like. Various sizes are utilized as well as cells which are intended for batch testing and some cells which are coupled for use with the so-called flow-through or continuous testing procedures. It is necessary in order to provide precise, accurate and repeatable results to effect the placement of the tubes or cells in a repeatably achievable orientation. It is necessary also to orient the cell so that the center line thereof intercepts and is perpendicular to the center line of the beam of light passed therethrough. Further, the desired cell position must be maintained notwithstanding the quantity of liquid in the cell or the size, type or configuration of the cell. Of course, the light beam must not be restricted in its passage through the cell.

There has been a long-felt need to provide cell holder constructions which are capable of positioning and maintaining the position of the cell where many different cell sizes and configurations can be utilized without appreciable change to the holding mechanism.

Another desirable attribute in addition to the capability of utilizing widely different sizes and configurations of cells, is the case of insertion of the cell into the holder with the avoidance of abrasion upon the outer wall thereof, so as to reduce the chances of scratching, marring or otherwise distorting the wall surfaces deleteriously affecting the optical properties of the cell.

SUMMARY OF THE INVENTION

A universal holder for objects such as test tubes, cuvettes, cells and the like comprising means defining a pair of upright oriented angular surfaces, pressure-exerting means including a biased member arranged spaced from said upright means, said pressure-exerting means being normally disposed between said angular surfaces and capable of being deflected by an object introduced between said angular surfaces and said pressure-exerting means, yet to maintain the object in erect condition therebetween.

DESCRIPTION OF PREFERRED EMBODIMENTS

Generally described, the invention herein is intended to position a cell or cuvette firmly so that a beam of light may be passed therethrough and the characteristics thereof measured such as encountered in the performance of photometric analytical procedures, for example. There is a housing which provides a chamber in which a light source can be disposed. At the opposite end of the housing, means are provided for mounting or otherwise positioning a photoresponsive device in a position to receive a beam of light from the light source subsequent to its passage through the cell or cuvette which is positioned as to intercept the beam. The means contemplated by the invention for positioning and maintaining the desired position of the cell comprise a stationary member which includes means defining surfaces which in turn define a V-shaped recessed into which the cell is placed, and a spring biased member arranged to bear upon the cell rigidly to hold the position thereof within the recess. The cell holder constructed in accordance with the invention is intended to accommodate cells of different, that is, varying, cross-sectional configurations and size, the minimum size being determined by the depth into which the bearing portions of the pivotable biased member enter the groove or recess with the maximum size being determined by the spacing between the pivot axis of the biased member and apex of the groove or recess as well as the angle at which the groove-defining surfaces join.

In order to accommodate cells of other than cylindrical configuration, such as the commonly encountered cells of rectangular cross section, at least one elongate notch is provided in each of the groove-defining surfaces. The notches so defined are coplanar with a vertical plane taken through the set of notches being normal to the light beam which is adapted to be passed through the cell. Passage means are provided in the stationary member to permit passage of the light beam uninterruptedly through the cell to the photoresponsive device.

The operation of the various embodiments of the invention, as will be described in detail hereinafter, is common, to wit, the cell or cuvette is introduced into the groove and bears against the biased member forcing same against its normal bias so that the biased member bears against the body of the cell. Sideway movement of the cell is prevented by the planar walls defining the groove while the vertical orientation of the cell is maintained by the biased member engaging the body of the cell. The light path is unobstructed in all instances. Where notches are provided in those planar surfaces defining the V-shaped groove, a cell having corners is held by the corners being seated within said notches.

Figure 1:
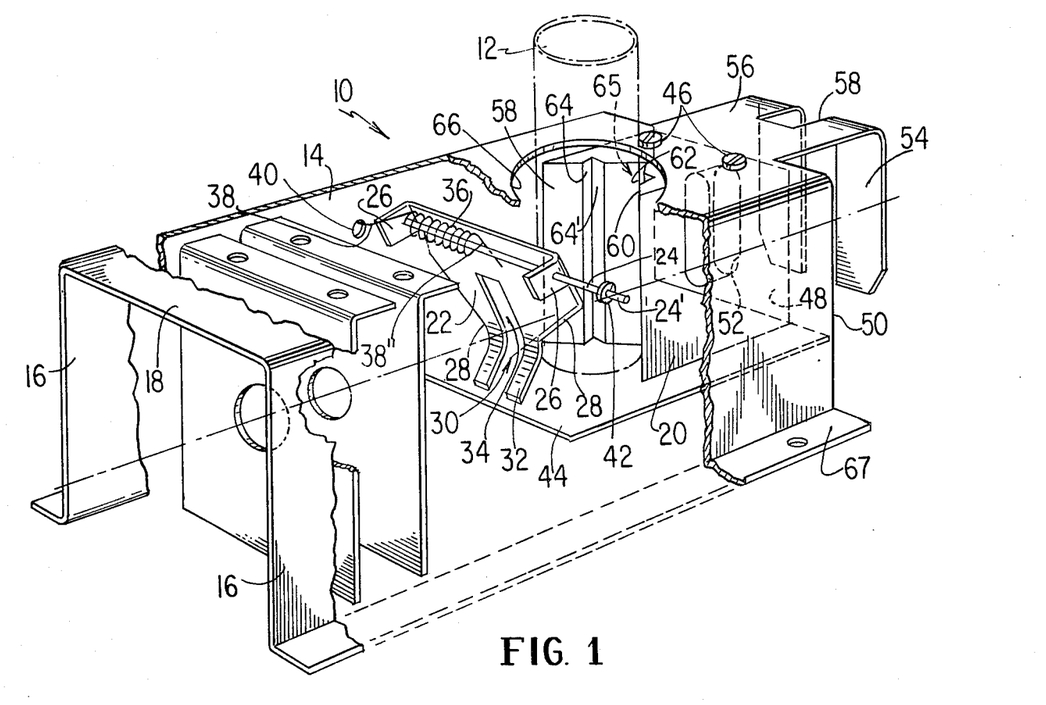
FIG. 1 is a perspective view of the cell holder constructed in accordance with the invention, portions being deleted to show the interior detail.

Referring now to FIG. 1, a universal cell holder, constructed in accordance with the invention, is designated generally by reference character 10 and is illustrated with a cell 12 of cylindrical configuration positioned thereby. Here, cell 12 is a round bottom, open-top test tube. The cell holder 10 includes an open-ended housing 14 of substantially U-shaped configuration defined by a pair of side walls 16 and a top wall 18. Within the housing there is a stationary body 20 and a plate member 22 arranged across the width of the housing spaced from body 20. The plate 22 is mounted for pivotal rotation on shaft 24. Plate 22 is of generally triangular planar configuration but including a pair of opposite ears 26 and a pair of diagonally extending side edges 28 converging to define an apex 30. A pair of downwardly depending arcuate fingers extend outwardly from the apex 30, the fingers being return bent at their termini. A slot 34 is formed in plate 22 opening to the apex 30 and is chosen to be of such length and configuration so as to permit an unobstructed passage of the light beam therepast when the plate 22 is urged to a condition normal to the wall 18, a condition where, absent the slot, the light beam path would be obstructed.

Figure 2:
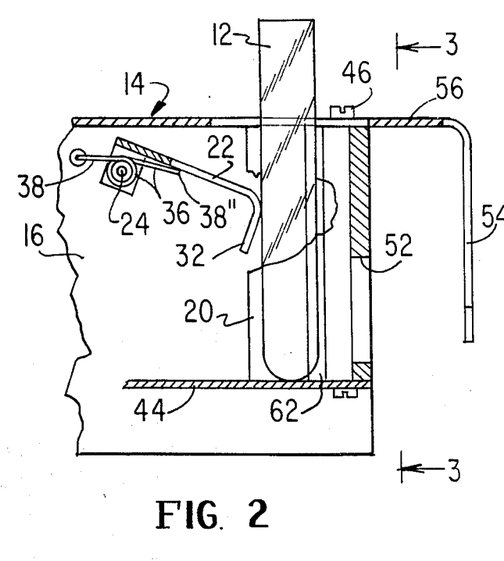
FIG. 2 is a side elevational view of the cell holder illustrated in FIG. 1, additional portions being deleted to show detail.
Figure 3:
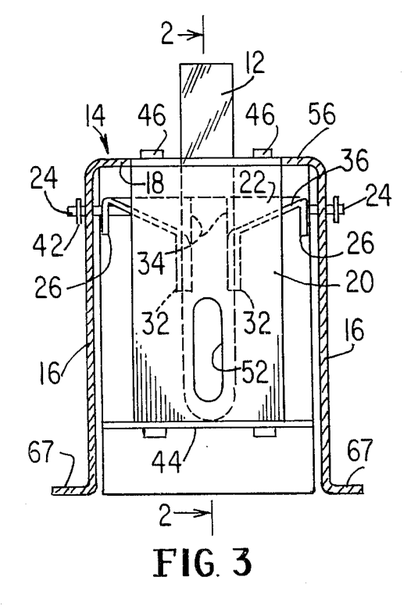
FIG. 3 is an end elevational view of the test tube holder of FIG. 1, portions being shown in section and other portions being broken away to show interior detail.

The shaft 24 passes through the coils of helical spring 26, the ends thereof disposed between ears 26. Spring 36 has an arm 38, one end 38' of which passes through a suitable opening 40 formed in the side wall 16 of the housing 14. The other end 38'' of spring 36 bears against the under surface of plate 22 as shown in FIG. 2. The shaft ends 24' are journaled in suitable openings formed in the side walls 16 of the housing 14 and are maintained by split rings 42. The plate 22 is biased by the spring 36 so as to be disposed normally horizontally in a plane substantially parallel to the top wall 18 of housing 14. The plate 22 can be moved pivotally against its normal bias by the action of cell 12 being forced between the fingers 32 of plate 22 and the planar walls defining the V-shaped group of body 20. The cell 12 pushes the plate 22 against its bias as it is urged toward plate 44. Plate 44 is secured as by screw means or the like to the bottom surface of body 20. The upper end of the body is secured to the top wall 18 of the housing as by screws 46. The body 20 has a rear surface 48 and is arranged so that surface 48 is flush with the open end 50 of the housing 14. The body 20 has a vertically oriented through slot 52 of size and configuration to provide a window to a photosensitive device (not shown) which is capable of being fastened to bracket arms 54 of mounting bracket 56. Mounting bracket 56 can be fastened to the housing 14 by the same screws as used to fasten the body 20. The mounting bracket 56 as shown is formed as an extension of the top wall 18.

The planar surfaces 58, 60 define a symmetrical V-shaped groove 62, the surfaces preferably being substantially at right angle one relative to the other. When the cell 12 is introduced into the groove 62, it pushes or bears upon the plate member 22 so as to move against its normal bias. The surfaces 58 and 60 act to restrict sideways movement of the cell 12 while the fingers 32 bear against the outer wall thereof. As will be noted in FIG. 1, a pair of notches 64 of angular configuration are formed in planar surfaces 58, 60. Walls 64' of notches 64 lie in the same vertical plane which is oriented parallel to the long axis of shaft 24 and normal to the optical path and bisects the angle of intersection of said surfaces 58, 60, which, as shown, is less than 180° the slots 34 and 52 are aligned and lie in a plane which bisects the angle of intersection of surfaces 58, 60.

The elongate outwardly extending flanges 64 are formed along side walls 16 and carry suitable passageways to permit mounting of the structure 10 to a platform (not shown). The arms 32 of plate 22 extend into the groove 62.

A circular opening 66 is formed in the top wall 18. The opening 66 has a diameter selected so that the apex 30 of the groove 62 lies along the circumference of the opening 66. The shaft 24 bridges the housing 14 at a location adjacent that edge 66 at a point diametrically opposite to the apex 30 of said groove 62.

Figure 4:
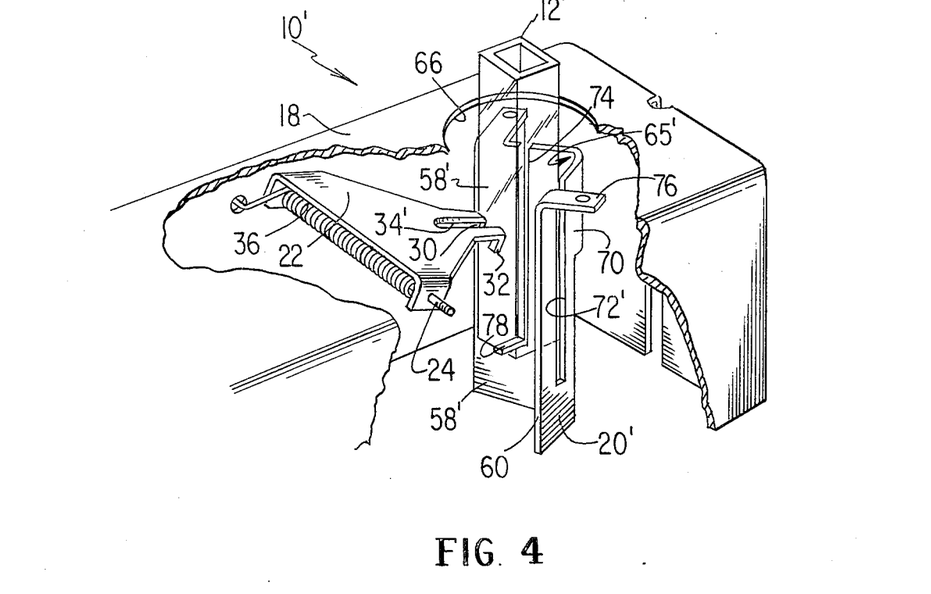
FIG. 4 is a perspective view of a modified embodiment of the invention, portions being broken away to show interior detail.
Figure 5:
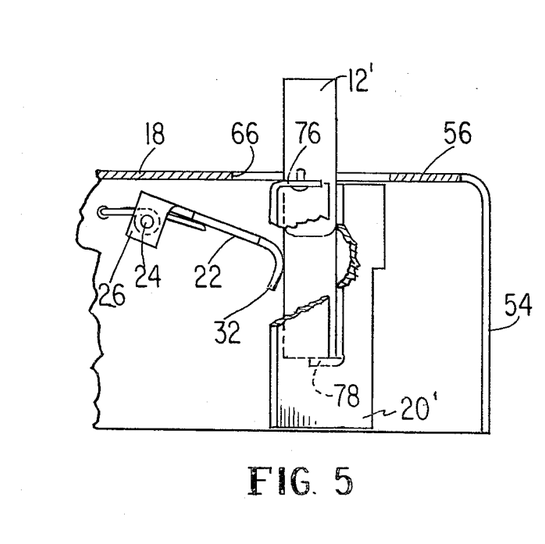
FIG. 5 is a side elevational view of the cell holder illustrated in FIG. 4, portions being broken away to show interior detail.
Figure 6:
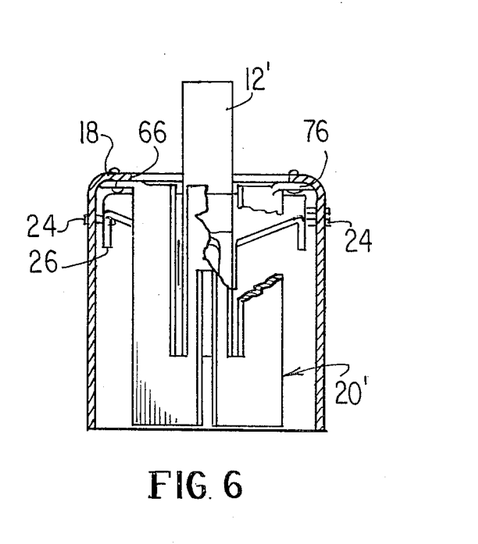
FIG. 6 is an end elevational view of the cell holder of FIG. 4, portions being shown in section portions broken away to show interior detail.

Referring to FIGS. 4 through 6, a modified embodiment of the invention is illustrated with the cell holder designated generally by reference character 10'. The cell holder 10' differs from cell holder 10 by the construction of the stationary member 20' in which the groove 62' equivalent to groove 62 is defined. The biased member 22 is utilized in the cell holder 10'.

The stationary member 20' comprises an upright metal plate which preferably is formed into the configuration shown as by stamping. A pair of legs 58' and 60' are joined at the upper ends by bridge 70. The bridge 70 is folded at substantially a 90 degree angle so as to define with the legs 58' and 60', the groove 62'. Elongate slots 72 and 74 are defined in the legs 58' and 60' respectively. These slots open to the upper edge of the body 20'. When the bridge 70 is formed at the angle indicated, the slots 72 and 74 intersect a vertical plane taken parallel to the axis of rotation of the shaft 24.

A pair of rearwardly directed right angle tabs 76 are provided which are integral with the upper edge of the legs 58' and 60' and fastening means (not shown) secure said tabs to the under surface of the top wall 18 of the housing 14.

In the holder 10' the platform 44 is omitted. The cuvette 12' is of a square cross-sectional configuration and is held seated within the groove 62' by the two-fold action of one of the arms 32 bearing against one wall of the cuvette 12' while the opposite corners of the cuvette 12' are disposed respectively in slots 72 and 74. The bottom corners of the cuvette 12' are seated on the ledges 78 which are defined at the innermost ends of slots 72 and 74 respectively.

Figures 7, 8:
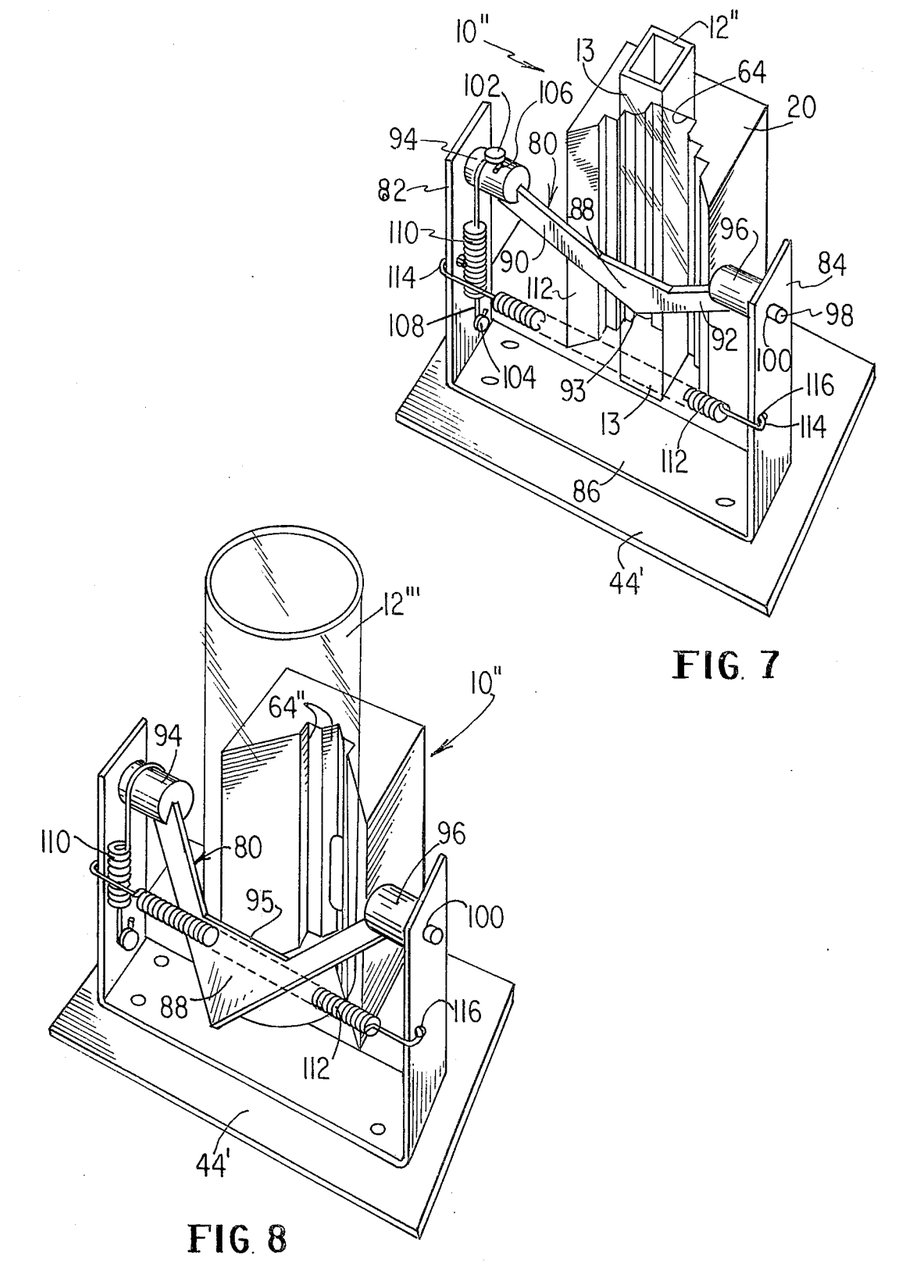
FIG. 7 is a perspective view of a still other modified embodiment of the invention.
FIG. 8 is a perspective view of the cell holder illustrated in FIG. 7 when utilized with a cell of other configuration.

Another modification of the invention is embodied in the holder 10'' illustrated in FIG. 7. Holder 10'' utilizes an upright body formation substantially the same as body 20 of FIG. 1. However, the biased member here has been modified and is designated generally by reference character 80. In addition, the housing has been omitted from the illustration, and may be omitted when the holder 10″ is employed. The member 80 is supported for pivotable rotation upon and between a pair of upright legs 82 and 84. The legs 82 and 84 are integral with a cross member 86 which is secured to a planar platform 44′ as by screw means, welding and the like.

Member 80 has a generally triangular portion 88 and a pair of arms 90 ad 92 which extend divergently in the same plane as portion 88 from the base of said triangular portion 88. The outer edges of the arms 90 and 92 effectively are continuations of the sides of triangular portion 88. The free ends of arms 90 and 92 are embedded in cylindrical bearing members 94 and 96. Coaxial extensions 98 are provided on bearing members 94 and 96. These extensions 98 are journaled in suitable conforming openings 100 formed in the legs 82 and 84. Openings 100 formed in legs 82 and 84 respectively are aligned. An upstanding button or hook 102 is provided on the circumferential surface of element 94. Likewise, an inwardly extending button 104 is provided on the inner facing surface of leg 82 adjacent its junction with plate portion 86. Both buttons 102 and 104 include a reduced diameter portion to provide a groove within which the ends 106 and 108 of spring 110 may be hooked.

With the spring 110 arranged vertically along the inner surface of leg 82, an expansion coil spring 112 is arranged axially parallel with the plate portion 86 and the platform 44′. The spring 112 is secured in bridging relationship to the legs 82 and 84 by hooks 114 passing through suitable openings 116 formed in the respective legs. The spring 112 acts to maintain the upright relationship of said legs and as well to maintain engagement of extensions 98 within openings 100.

In FIG. 7, the rectangular cell 12″ is seated in the notches 64 of the stationary upright member 20. The apex 93 of member 88 is engaged in a point contact with one wall 13 of cell 12″. At this location, the portion 88 does not obstruct relative the light beam.

In FIG. 8, however, a large cylindrical cuvette 12′″ is illustrated in the cell holder 10″ but here, the edge 95 of portion 88 engages the cylindrical body of enlarged cylindrical cell 12′″, with the arm rotated an additional arc so that the spring 112 is disposed between member 80 and the tube 12′″. Thus, the spring 112 additionally functions to maintain the position of the cuvette 12′″.

Figure 9:
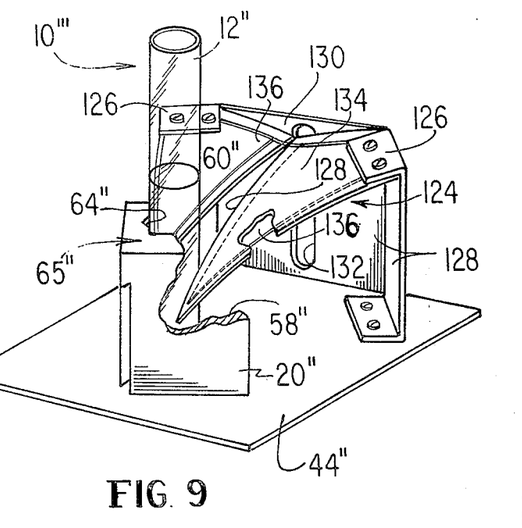
FIG. 9 is a perspective view of a still further modified embodiment of the invention.
Figure 10:
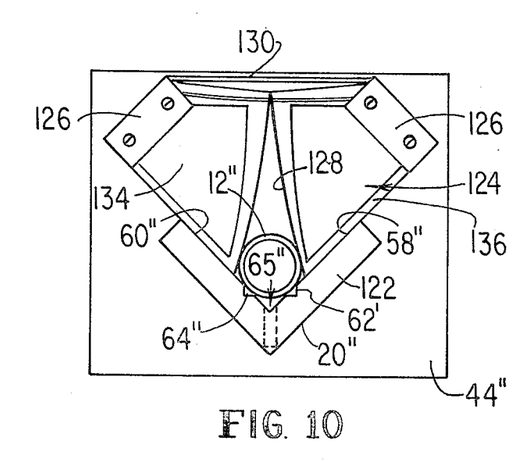
FIG. 10 is a top plan view of the cell holder illustrated in FIG. 9.
Figure 11:
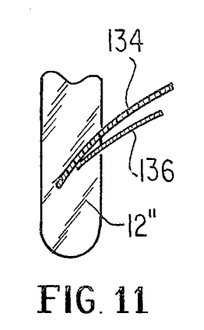
FIG. 11 is a diagrammatic representation of a detail of the cell holder illustrated in FIGS. 9 and 10.

Referring now to FIGS. 9 through 11, another modified embodiment of the invention is designated generally by reference character 10′″ and comprises a body 20″ carrying V-shaped groove 62″. The groove 62″ is defined by the inner walls 58″ and 60″ of right-angle arranged upright portions 120 and 122. Notches 64″ are provided in the angle-defining surfaces 58″ and 60″.

Spring means designated generally by reference character 124 are arranged to engage and bias the cell 12″ in an upright condition within the V-shaped groove 62″. The spring means 124 comprise a pair of double-layered spring leaves 134 and 136 having curved, facing inner edges 128. The springs 124 are secured to angled tabs 126 formed at the upper ends of upstanding bracket 128. The bracket 128 is secured to the platform 44″ and includes a bridging wall 130 arranged perpendicular to the platform 44″. An elongate slot 132 is formed in said wall 130. The body 20″ carries a slot 52′ located in alignment with slot 132 whereby to provide an unobstructed path for the light beam intended to be passed through the cell 12.

The spring means 124 is defined by an upper leaf 134 preferably formed of plastic material, and a metal leaf 136 which serves as a support for the upper leaf. The metal leaf is smaller than the leaf 134, the edges thereof being spaced inwardly of the outer edges of leaf 134 so that the actual contact with the body of cuvette 12 is effected by the plastic leaf 134, that is, the edge of said plastic leaf. The metal leaf 136 preferably is formed of a spring metal sufficiently resilient to apply sufficient bias to the plastic leaf to enable the contact with the body of cylindrical cuvette 12 to be firm.

The cell 12 is inserted downwardly into the groove 62″ and between the spring leaves 124, spreading the same. The edges of the leaves 134 contact the cylindrical body of cuvette 12 and force said cuvette in erect upright orientation within the groove 62″.

Although the universal cell holders embodying the invention have been described in terms of their application to photometric procedures, the invention contemplates their applicability for use as a vessel support useful for the performance of other procedures upon the contents of such vessels, and hence is not limited merely to utilization for photometric procedures.

What it is desired to be secured by Letters Patent of the United States is:

1. A universal cell holder comprising upright means defining a pair of upright oriented angular surfaces occupying intersecting vertical planes defining a V formation, deflectable pressure exerting means including at least one spring-biased arm having a free end normally disposed directed on a generally horizontal plane toward the interior apex of said V formation, mounting means vertically offset from said angular surfaces mounting said arm for pivotal movement about an axis spaced from said upright means, means biasing said pressure exerting means to assume said normal disposition within said V-formation and across the path of an object introduced between said angular surfaces and said pressure exerting means along a path taken vertically within said V-formation, said pressure exerting means being interceptible and deflectable by passage of said object, said pressure exerting means being moved in a direction outward of said V-formation displacing the said free end yet retaining a positive, minimum contact, bearing engagement therewith maintaining the said object upright between said angular surfaces and said pressure exerting means.

2. The universal cell holder as claimed in claim 1 in which said upright means comprise a unitary elongate block member of substantially rectangular cross section and a lengthwise extending substantially V-shaped recess formed in said block opening toward said pressure exerting means, said free end normally entering said recess and extening to a location adjacent the interior apex thereof.

3. The universal cell holder as claimed in claim 1 in which the angle of intersection of said intersecting planes is less than 180°.

4. A universal cell holder comprising upright means defining a pair of upright oriented angular surfaces occupying intersecting vertical planes defining a V formation, deflectable pressure exerting means including at least one spring-biased arm having a free end normally disposed directed toward the interior apex of said V formation, mounting means vertically offset from said angular surfaces mounting said arm for pivotal movement about an axis spaced from said upright means, means biasing said pressure exerting means to assume said normal disposition within said V-formation and across the path of an object introduced between said angular surfaces and said pressure exerting means along a path taken vertically within said V-formation, said pressure exerting means capable of being deflected by passage of said object while retaining a positive, minimum contact, bearing engagement therewith maintaining the said object upright between said angular surfaces and said pressure exerting means, said defectable pressure exerting means comprising a generally triangular arm member mounteed for pivotal rotation about an axis taken along the base of said member, and said biasing means being coupled to said triangular arm member to dispose the sides thereof between said angluar surfaces whereby to intercept the object introduced between said upright means and said triangular arm member, said triangular arm member being deflectable by said object with the triangular arm member in minimum contact bearing engagement with said object thereafter.

5. The universal cell holder as claimed in claim 4 in which the angle of intersection of said intersecting planes is less than 180°, means defining a through radiation beam path along a line bisecting the angle of intersection of said intersecting planes, the said means including a slot formed in the upright means at a location aligned with a plane taken vertically through said bisecting line.

6. The universal cell holder as claimed in claim 1 in which matched notch means are provided in said angular surfaces, said matched notch means including coplanar walls lying in a plane taken at right angle to the plane bisecting the angle of intersection of said surfaces, said notch means adapted to seat at least two corners of an object introduced between said surfaces which includes walls defining such corners.

7. A universal cell holder comprising upright means defining a pair of upright oriented angular surfaces occupying intersecting planes, deflectable pressure exerting means including at least one biased arm arranged spaced from said upright means, means biasing said pressure exerting means for normal disposition between said angular surfaces, said pressure exerting means capable of being deflected by an object introduced between said angular surfaces and said pressure exerting means and maintaining the cell erect therebetween, said deflectable pressure exerting means including at least a pair of biased arms, means mounting said arms so as to dispose the same between said angular surfaces and said biased arms comprise, a pair of spring leafs arranged to be disposed with the tips thereof between said angular surfaces and said spring leafs having facing edge surfaces of relatively divergent curvilinear conformation, each spring leaf capable of being deflected to increase the spacing therebetween upon introduction of the object between the said angular surfaces.

8. The universal cell holder as claimed in claim 7 in which said upright means comprises a pair of angularly disposed, vertical walls and a bridging wall therebetween, means defining a vertically extending elongate slot in said bridging wall and means defining a passage through the intersection of said angular surfaces, said passae being aligned with said slot.

9. A universal cell holder for positioning a cell body in upright relationship substantially normal to and intercepting an optical path, said cell holder comprising:
a platform,
wall means defining an upright angular formation,
means securing said formation to said platform,
deflectable holding means for engaging the exterior of the cell body wall when the cell body is positioned within said angular formation and against the wall means,
means spaced vertically from said wall means for pivotably mounting said holding means,
biasing means coupled to said holding means for urging said holding means in a normal position extending in a generally horizontal plane within said angular formation,
said holding means being interceptible and deflectable against said bias by a cell body introduced within said angular formation and between said formation and said holding means to move same from said normal position in a direction outward of said formation while maintaining a positive minimum area bearing engagement with said cell body, and
means defining a through optical path along a line taken through the apex of said angular formation along a line bisecting the angle thereof.

10. The structure as claimed in claim 9 in which said angular formation is V-shaped with the apex of the V aligned with the optical path and said path being normal to the central axis of said upright maintained cell body, said holding means extending normally to a location closely adjacent the interior of the apex of said angular formation.

11. The structure as claimed in claim 9 in which said wall means are defined by an upright body having angular facing surfaces arranged to form a "V" recess, the intersection of said surfaces being located in alignment with the optical path and said optical path defining means include slot means formed at said intersection.

12. The structure as claimed in claim 11 in which said upright body is generally solid and said V-shaped recess opens toward said deflectable holding means.

13. A universal cell holder for positioning a cell body in upright relationship substantially normal to and intercepting an optical path, said cell holder comprising:
a platform,
wall means defining an upright angular formation,
means securing said formation to said platform,
deflectable holding means for engaging the exterior of the cell body wall when the cell body is positioned within said angular formation and against the wall means,
means spaced vertically from said wall means for pivotably mounting said holding means,
biasing means coupled to said holding means for urging said holding means in normal position within said angular formation,
said holding means being deflectable against said bias by a cell body introduced within said angular formation and between said formation and said holding means, and
means defining a through optical path along a line taken through the apex of said angular formation along a line bisecting the angle thereof, said deflectable holding means comprising a spring biased member of essentially triangular configuration mounted for pivotal movement about the base thereof with the apex extending within the recess defined by said upright angular formation.

14. A universal cell holder comprising:
an upright support having a side opening generally V-shaped recess extending along the length and opening at the upper end thereof to define an entrance,
means for biasing a cell against said support and within the recess, and said biasing means comprise a planar deflectable member of generally triangular configuration including a pair of opposite end tabs adjacent the base thereof,
shaft means arranged to extend along the base of said planar member and seated in openings formed in said tabs,
spring means mounted on said shaft means and having an end arm, one end secured to said support and the other in bearing relation with a major surface of said member thereby biasing said member to a generally horizontal disposition relative to said upright support with at least a portion of said planar member entering said recess.

15. The structure as claimed in claim 14 and means defining an optical path taken through the apex of said V-shaped recess along the line bisecting said recess and normal to the long axis of said cell.

16. The cell holder as claimed in claim 14 in which said support is a framework including at least two intersecting surfaces defining said recess and said biasing means comprising a spring biased deflectable member having an end portion extending within said recess, the cell capable of being introduced into said recess by way of said entrance and deflecting said deflectable member.

17. The cell holder as claimed in claim 14 and slot means arranged to allow free passage of a radiation beam in a direction normal to the axis of the cell and aligned with a plane bisecting the angle of intersecting of said surfaces.

18. The universal cell holder as claimed in claim 14 in which aligned slot means are defined in said upright support and said deflectable member to provide free passage of a beam of light therethrough in a direction normal to the axis of said cell.

19. The cell holder as claimed in claim 18 in which said upright member includes a pair of intersecting surfaces disposed along a pair of intersecting planes with a line bisecting the angle of intersection being coplanar with said light beam path and aligned with said slot means.

20. The cell holder as claimed in claim 14 in which said defectable member is formed of generally triangular configuration having a pair of divergently extending coplanar arms and a straight edge therebetween.

21. The cell holder as claimed in claim 14 and plural notch means formed in said recess defining surfaces for receiving cells having corner defining walls.

22. The cell holder as claimed in claim 14 and slot means formed in said recess defining surfaces for receiving adjacent corner walls of a cell.

23. The cell holder as claimed in claim 14 in which said surfaces lie in a pair of vertically oriented intersecting planes defining an angle of intersection less than 180°,
first slot means formed in said support at said intersection,
second slot means formed in said biasing means aligned with said first slot means along a line bisecting the angle of intersection.

24. A universal cell holder comprising:
an upright support having a side opening generally V-shaped recess extending along the length and opening at the upper end thereof to define an entrance,
means for biasing a cell against said support and within the recess, said support comprising a framework including at least two intersecting surfaces defining said recess and said biasing means comprising a spring biased deflectable member extending within said recess, the cell capable of being introduced into said recess by way of said entrance and deflecting said deflectable member, said surfaces having a pair of top opening elongate slots formed therein, the inner ends of said slots being opposite one another and lying in a plane taken normal to a plane bisecting the angle of intersection of said surfaces.

25. A universal cell holder comprising:
an upright support having a side opening generally V-shaped recess extending along the length and opening at the upper end thereof to define an entrance, means for biasing a cell against said support and within the recess, said biasing means comprise
deflectable member including at least two angularly extending convergently directed coplanar leaf members having their narrow ends entering said recess and their adjacent edges curved divergently one from the other, and
leaf spring means underlying said leaf members, the edges of said spring means being spaced from the peripheral edges of said leaf members.

26. A universal cell holder comprising:
an upright support having a side opening generally V-shaped recess extending along the length and opening at the upper end thereof to define an entrance, and
means for biasing a cell against said support and within the recess, said upright support comprising a vertically oriented bracket member including upstanding side walls angularly disposed and having upper tab means and said biasing means comprising a pair of double layered spring leaves secured respectively to said tab means and terminating within said recess, said leaves adapted to be deflected downwardly by introduction of the cell therebetween and within said recess.

27. A universal cell holder for positioning a cell of generally elongate tubular configuration disposed substantially perpendicular to a light beam comprising:
a housing including a top wall and a pair of parallel side walls,
the top wall having a passageway for receiving a cell therethrough,
support wall means arranged generally vertically within said housing and including an elongate side opening recess and having an entrance at the upper end thereof,
biased engaging means including a free end arranged in facing relation to said recess and mounted for pivotable movement about an axis spaced from said recess from a normal disposition with at least its free end extending substantially interior of the recess to a displaced disposition against said bias and engaging the cell body in at most a line contact bearing engagement with the cell body when the cell body is introduced into said passageway between said engaging means and the support wall means and held thereby against said support wall means within said recess.

28. A universal holder for orienting selected objects of differing size and shape in a fixed disposition relative to a path, said holder comprising:
  means defining at least a pair of object engaging planar surfaces angularly arranged in a pair of intersecting vertically oriented planes,
  deflectable arm means mounted for rotation along a path traversing the area between said surface,
  biasing means coupled to said arm means for disposing said arm means between said surfaces,
  said arm means capable of being intercepted and deflected by an object introduced between said surfaces to displace said arm means away from said surfaces yet maintaining at most a line contact positive engagement with said object to hold said object against said surfaces.

29. The holder as claimed in claim 28 in which said means defining said surfaces comprise a pair of generally flat upright oriented walls defining a V-shaped recess opening to said arm means and positioned to receive same therebetween.

30. The holder as claimed in claim 29 in which said walls are defined by an upright arranged angular bracket.

31. The holder as claimed in claim 29 in which there are parallel facing notch means formed in said surfaces lengthwise thereof, said notch means capable of receiving adjacent corners of an object.

\* \* \* \* \*

UNITED STATES PATENT AND TRADEMARK OFFICE
CERTIFICATE OF CORRECTION

PATENT NO. : 3,977,794
DATED : August 31, 1976
INVENTOR(S) : GERHARD A. LIEDHOLZ It is certified that error appears in the above-identified patent and that said Letters Patent are hereby corrected as shown below:

Col. 2, line 50, change "recessed" to --recess--;
col. 3, line 45, change first occurrence of "26" to --36--;
col. 4, line 10, after "move" insert --same--;
col. 5, line 11, change "ad" to --and--; col. 7, line 68 change "passae" to --passage--; col. 10, line 28, change "member" to --members--

Signed and Sealed this

Nineteenth Day of April 1977

[SEAL]

Attest:

RUTH C. MASON
Attesting Officer

C. MARSHALL DANN
Commissioner of Patents and Trademarks